(12) United States Patent
Cohen et al.

(10) Patent No.: US 7,875,066 B2
(45) Date of Patent: Jan. 25, 2011

(54) THERMAL GRILL FOR HEATING ARTICLES

(75) Inventors: Jason C. Cohen, Appleton, WI (US);
Eric Donald Johnson, Larsen, WI (US);
Michael Joseph Garvey, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1079 days.

(21) Appl. No.: 11/636,820

(22) Filed: Dec. 11, 2006

(65) Prior Publication Data
US 2008/0140165 A1 Jun. 12, 2008

(51) Int. Cl.
*A61F 7/00* (2006.01)
*A61F 7/08* (2006.01)
(52) U.S. Cl. .......................... 607/108; 607/96; 607/114
(58) Field of Classification Search .................. 607/108
See application file for complete search history.

(56) References Cited

U.S. PATENT DOCUMENTS

| | | | |
|---|---|---|---|
| 2,602,302 A * | 7/1952 | Poux ............................ | 62/530 |
| 3,132,688 A | 5/1964 | Nowak | |
| 3,175,558 A | 3/1965 | Caillonette et al. | |
| 3,463,161 A | 8/1969 | Andrassy | |
| 3,900,035 A | 8/1975 | Welch et al. | |
| 4,462,224 A | 7/1984 | Dunshee et al. | |
| 4,585,002 A | 4/1986 | Kissin | |
| 4,596,250 A | 6/1986 | Beisang, III et al. | |
| 4,704,116 A | 11/1987 | Enloe | |
| 4,781,193 A | 11/1988 | Pagden | |
| 4,798,603 A | 1/1989 | Meyer et al. | |
| 4,860,748 A | 8/1989 | Chiurco et al. | |
| 4,886,063 A | 12/1989 | Crews | |
| 4,940,464 A | 7/1990 | Van Gompel et al. | |
| 4,981,135 A | 1/1991 | Hardy | |
| 5,167,655 A | 12/1992 | McCoy | |

(Continued)

FOREIGN PATENT DOCUMENTS

EP 1 263 379 B1 10/2004

(Continued)

OTHER PUBLICATIONS

Bouhassira, Didier et al., "Investigation of the Paradoxial Painful Sensation ('Illusion of Pain') Produced by a Thermal Gril," *Pain*, International Association for the Study of Pain, published by Elsevier, vol. 114, 2005, pp. 160-167.

(Continued)

*Primary Examiner*—Roy D Gibson
*Assistant Examiner*—Kaitlyn E Helling
(74) *Attorney, Agent, or Firm*—Randall W. Fieldhack

(57) ABSTRACT

The present disclosure provides an article adapted to produce heat, the article including an outer surface having a skin-facing surface, the outer surface enclosing a heat generator; and a thermal grill disposed on the skin-facing surface. The present disclosure also provides an article for delivering a heating sensation, the article including a skin-facing surface; a plurality of warm portions disposed on the skin-facing surface; and a plurality of cool portions disposed on the skin-facing surface, wherein the warm portions and cool portions are disposed in an alternating pattern.

28 Claims, 3 Drawing Sheets

U.S. PATENT DOCUMENTS

| | | | |
|---|---|---|---|
| 5,176,672 | A | 1/1993 | Bruemmer et al. |
| 5,266,592 | A | 11/1993 | Grub et al. |
| 5,348,750 | A | 9/1994 | Greenberg |
| 5,415,624 | A | 5/1995 | Williams |
| 5,486,166 | A | 1/1996 | Bishop et al. |
| 5,490,846 | A | 2/1996 | Ellis et al. |
| 5,509,915 | A | 4/1996 | Hanson et al. |
| 5,545,197 | A | 8/1996 | Bowen |
| 5,628,769 | A | 5/1997 | Saringer |
| 5,649,914 | A | 7/1997 | Glaug et al. |
| 5,702,376 | A | 12/1997 | Glaug et al. |
| 5,766,389 | A | 6/1998 | Brandon et al. |
| 5,785,980 | A | 7/1998 | Mathewson |
| 5,792,213 | A | 8/1998 | Bowen |
| 5,797,892 | A | 8/1998 | Glaug et al. |
| 5,820,973 | A | 10/1998 | Dodge, II et al. |
| 5,993,433 | A | 11/1999 | St. Louis et al. |
| 6,096,067 | A | 8/2000 | Cramer et al. |
| 6,165,208 | A | 12/2000 | Reyes et al. |
| 6,248,097 | B1 | 6/2001 | Beitz et al. |
| 6,248,125 | B1 | 6/2001 | Helming |
| 6,308,341 | B1 | 10/2001 | Shelton |
| 6,567,696 | B2 | 5/2003 | Voznesensky et al. |
| 6,645,190 | B1 | 11/2003 | Olson et al. |
| 6,648,909 | B2 | 11/2003 | Helming |
| 6,658,432 | B1 | 12/2003 | Alavi et al. |
| 6,770,064 | B1 | 8/2004 | Ruscher |
| 6,791,004 | B2 | 9/2004 | Sprengard-Eichel et al. |
| 6,869,441 | B2 | 3/2005 | Agarwal et al. |
| 6,881,219 | B1 | 4/2005 | Agarwal et al. |
| 7,083,839 | B2 | 8/2006 | Fish et al. |
| 7,321,309 | B2 * | 1/2008 | Cohen ............ 340/573.1 |
| 2004/0127880 | A1 | 7/2004 | Weber |
| 2006/0142828 | A1 | 6/2006 | Schorr et al. |
| 2006/0178717 | A1 | 8/2006 | Harris et al. |
| 2006/0236998 | A1 | 10/2006 | Cohen |
| 2006/0238359 | A1 | 10/2006 | Cohen |
| 2008/0045913 | A1 * | 2/2008 | Johnson et al. ............ 604/361 |

FOREIGN PATENT DOCUMENTS

| | | |
|---|---|---|
| WO | WO 00/37009 A2 | 6/2000 |
| WO | WO 01/10366 A1 | 2/2001 |
| WO | WO 01/26499 A1 | 4/2001 |
| WO | WO 01/26527 A1 | 4/2001 |
| WO | WO 01/26528 A1 | 4/2001 |
| WO | WO 01/26530 A1 | 4/2001 |
| WO | WO 01/27239 A1 | 4/2001 |
| WO | WO 02/064069 A2 | 8/2002 |
| WO | WO 03/094644 A1 | 11/2003 |
| WO | WO 2004/043311 A1 | 5/2004 |
| WO | WO 2004/084782 A1 | 10/2004 |
| WO | WO 2005/018514 A1 | 3/2005 |

OTHER PUBLICATIONS

Craig, A.D. and M.C. Bushnell, "The Thermal Grill Illusion: Unmasking the Burn of Cold Pain," *Science*, vol. 265, Jul. 8, 1994, pp. 252-255.

* cited by examiner

THERMAL GRILL FOR HEATING ARTICLES

BACKGROUND

Some aspects of the disclosure relate to a system for delivering heating for therapeutic and/or comfort purposes, and in particular to a system for improving the perceived heat availability of heating systems.

Applying therapy to various parts of a body is a recognized practice for curing or alleviating multiple kinds of physical problems. One example therapy applies heat to an area of a body using a heating pad to treat symptoms such as stiffness, muscle pain, cold hands and feet, lumbago, rheumatism, and neuralgia, among others.

One concern with using heating pads or patches to apply therapy is that they are often slow to rise to their effective temperature. A typical heat patch generates heat via either an exothermic reaction that takes place within the heat patch, or an exothermic electrical resistive heating, but that exothermic heat source is not immediately felt. Heat patches that generate heat using an exothermic heat source usually include an enclosure and a heating source that is stored within the enclosure. For the case in which the heating source is a chemical composition, at least one section of the enclosure can be air-permeable such that exposing the heating composition to air generates an exothermic reaction that increases the temperature of the heat patch.

In addition, many articles intended for personal wear, e.g., such as feminine hygiene products, adult incontinence products, bandages, medical garments and the like are designed to be sufficiently absorbent to pull moisture from liquid body exudates including urine, menses, blood, etc. away from the wearer. Because of the nature of such products, the skin areas to which they are commonly applied are often sensitive, leading to the feeling that the products are cool or cold upon initial application. In addition, other commonly-used products intended to be used in proximity to an individual's skin may also feel cool or cold upon initial application or use.

SUMMARY

Consequently, while there has been progress in the design of personal wear articles and other articles that provide heat that are intended to come into contact with a subject's skin, there continues to be a need for improvements in such articles. What is needed is a device that provides an instant-on heating sensation until either a heat source heats sufficiently, or until the user's body heats a product sufficiently to be comfortable. A thermal grill in conjunction with a heat patch or a personal wear article provides such instant-on heating.

A thermal grill is a device that includes interlaced or alternating warm and cool portions that are able to cause a sensation of heat to an individual when the individual touches the interlaced warm and cool portions. The relative size, shape, design, configuration, temperature, and orientation of the interlaced warm and cool portions may be varied to adjust the level of perceived heat that can be generated within an individual who touches the thermal grill with their skin.

A sensation of heat is elicited within an individual when the individual touches interlaced warm and cool bars with their skin.

One of the prevailing explanations of this heat sensation is that the perception of "heat" is a fusion of sensations resulting from simultaneous activation of warm and cool sensors within the body. Modern physiological findings have confirmed the existence of separate cutaneous receptors for warm and cool. It is interesting to note that the cutaneous receptors that are associated with a cold sensation appear to be activated by low and high temperatures.

The present disclosure relates to a heating system for delivering a perception of heat in articles intended to be used near or applied to a subject's skin. In one aspect, the heating system includes a thermal grill that may be used to deliver a heating sensation to an individual when the individual activates the thermal grill.

More specifically, the present disclosure includes an article adapted to produce heat, the article including an outer surface having a skin-facing surface, the outer surface enclosing a heat generator; and a thermal grill disposed on the skin-facing surface.

In addition, the present disclosure includes an article for delivering a heating sensation, the article including a skin-facing surface; a plurality of warm portions disposed on the skin-facing surface; and a plurality of cool portions disposed on the skin-facing surface, wherein the warm portions and cool portions are disposed in an alternating pattern.

Also, the present disclosure includes a method for generating a perception of heating from a skin-contacting article, the method including producing a skin-contacting article having a skin-facing surface; and disposing a thermal grill on the skin-facing surface.

Also, the present disclosure includes a method for providing a system of articles, the method including providing a first article having a first thermal grill exhibiting a first level of heat perception delivery when activated; and providing a second product having a second thermal grill exhibiting a second level of heat perception delivery when activated, wherein the second level of heat perception delivery is greater than the first level of heat perception delivery.

Also, the present disclosure includes a method for providing heat to an individual, the method including providing an article having an outer surface and a body adapted to produce long-term heating; and providing a thermal grill disposed on the outer surface, wherein the thermal grill is adapted to produce an instant-on sensation of heat.

The purposes and features of the present disclosure will be set forth in the description that follows. Additional features of the disclosure may be realized and attained by the product and processes particularly pointed out in the written description and claims hereof, as well as from the appended drawings.

It is to be understood that both the foregoing general description and the following detailed description are exemplary and are intended to provide further explanation of the disclosure claimed. The accompanying drawings, which are incorporated in and constitute part of this specification, are included to illustrate and provide a further understanding of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

Figure 1:
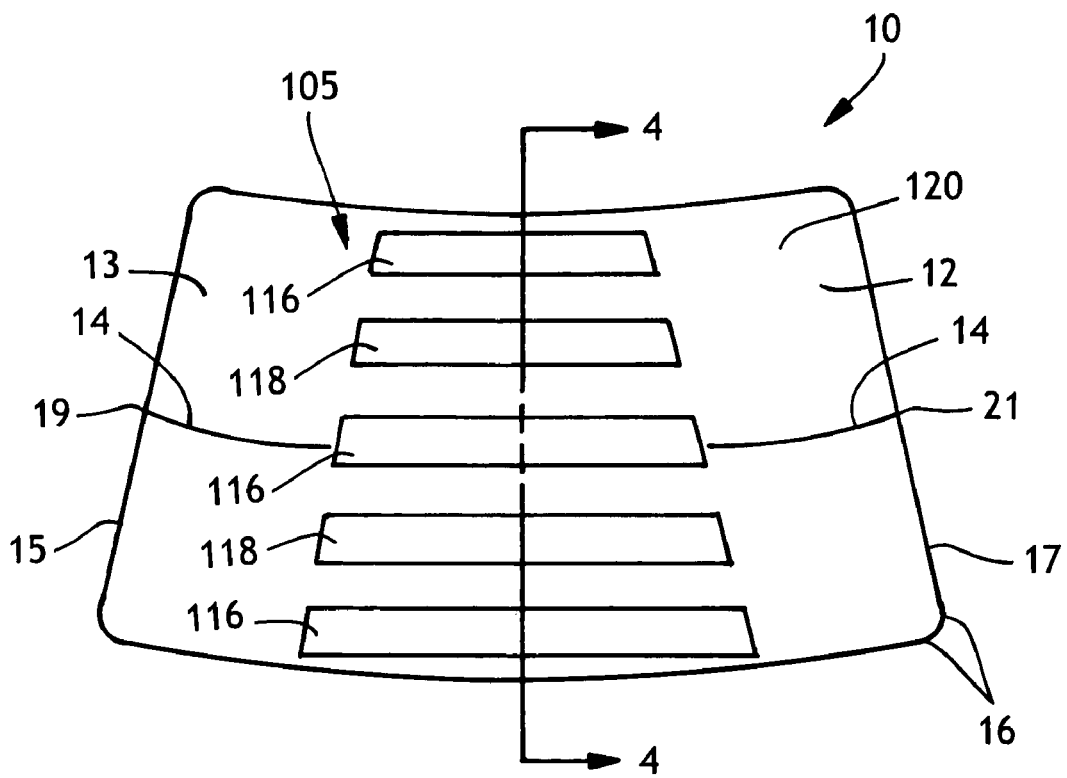
FIG. 1 is a plan view of an example article for providing therapy to an individual.

Repeat use of reference characters in the present specification and drawings is intended to represent the same or analogous features or elements of the present disclosure. The drawings are representational and are not necessarily drawn to scale. Certain proportions thereof may be exaggerated, while others may be minimized.

DETAILED DESCRIPTION OF THE DISCLOSURE

The following detailed description references the accompanying drawings that show some example aspects of the disclosure. These example aspects are described in sufficient detail to enable those skilled in the art to practice the disclosure. It is to be understood that other aspects may be utilized, or structural changes made, such that the detailed description should not be considered as limiting the scope of the claims.

As used herein, a "thermal grill" is a device that includes interlaced warm and cool portions, where the temperature difference between the interlaced warm and cool portions causes an individual to feel heat when the individual touches the thermal grill but does not cause physiological effects to the individual (the "thermal grill effect"). It should be noted that not causing physiological effects means that the stimuli that is provided by the thermal grill can not cause injury to an individual that touches the thermal grill with their skin.

As used herein, the term "warm portion" and its plural refer to the portion of the thermal grill that is exothermic or potentially exothermic. As used herein, exothermic refers to emitting heat and such heat can be created by a chemical reaction, by electrically-resistive heating, by warmed fluid, or by any other suitable means. The "warm portion" may actually feel warm as it does upon activation, or the "warm portion" may be potentially warm or warmable as it is before activation in that it includes material that will give off heat upon activation. Likewise, as used herein, the term "cool portion" and its plural refer to the portion of the thermal grill that is endothermic or potentially endothermic. The "cool portion" may actually feel cool as it does upon activation, or the "cool portion" may be potentially cool or coolable as it is before activation in that it includes material that will absorb heat upon activation.

The interlaced warm and cool portions may be a variety of sizes, designs, configurations, shapes, temperatures, and orientations as long as the thermal grill generates a perception of heat or discomfort within an individual without physiologically damaging the individual when the individual touches the thermal grill. The relative size and shape of the interlaced warm and cool portions that form the thermal grill will depend on the applications where the thermal grill is used.

Without committing to a particular theory, it is generally the case that the greater the temperature difference between the warm and cool portions, the greater the probability that the wearer will experience consequential discomfort. A temperature difference in the range of 5-10° C. is where a discomfort response typically begins to be experienced. At higher temperature differences, the intensity of the discomfort response and the percent of wearers who will have a discomfort response increases (see Bouhassira, et al, "Investigation of the Paradoxical Painful Sensation ('Illusion of Pain') Produced by a Thermal Grill"—Pain 114 (2005) 160-167).

Similarly, the width and spacing of the warm and cool portions in the thermal grill may be varied to vary the discomfort response. One source points to a preferable arrangement of 1 cm alternating stripes with a spacing between stripes of 3 mm. (see Craig and Bushnell "The Thermal Grill Illusion: Unmasking the Burn of Cold Pain"—Science Vol. 265, 8 Jul. 1994).

The thermal grill effect is a tactile thermal effect that produces the sensation of heat by presenting interlaced warm (e.g. 40° C.) and cool (e.g. 20° C.) portions. The warm and cool portions themselves do not elicit an elevated temperature response and are not damaging to the skin. At lower temperature differences between warm and cool portions, there is an increased perception of warmth/heat. Applying the tactile thermal grill effect with the difference in temperature between the warm and cool portions being below the pain threshold elicits an enhanced warming perception. By providing alternating warm and cool portions that are at a small temperature difference (around 10° C. or less), few subjects report pain and instead experience a perception of increased warmth perception.

The thermal grill effect can be leveraged to enhance the perception of warming from or a warm temperature of virtually any product, including heating pads, hand warmers, heat therapy devices, warm-up clothing, hats and other head coverings, foot warmers, patches, bands, and pouches; other clothing; car seats and car seat covers; strollers and other baby products; spa products, towels such as those provided by airlines, restaurants, and beauticians; bedding and upholstery; clothing and shoes; toilet seat covers; personal care and related products including diapers, training pants, swim pants, feminine hygiene products, incontinence products, medical garments, surgical pads and bandages; other personal care or health care garments; and virtually any other article, product, or garment that is a skin-contacting article that will come in contact with a subject's skin without departing from the scope of the present disclosure. The thermal grill provides an instant-on effect in the case of products that are intended to heat the subject but would otherwise take time to rise to a sufficient temperature, and a warm and perhaps cozy effect in products that would otherwise feel unpleasantly cool when exposed to skin.

In a specific but non-limiting example of the use of a thermal grill to provide or enhance the perception of heat, and referring to FIG. 1, an article 10 in the form of a patch for providing therapy to an individual is shown. The article 10 may or may not be disposable, and includes a body 12 that applies therapy to the individual when the article 10 is placed on the individual. The body 12 includes and is enclosed by an outer surface 13. In one aspect of the present disclosure, the article 10 may further include at least one cut 14 in the body 12.

Figure 2:
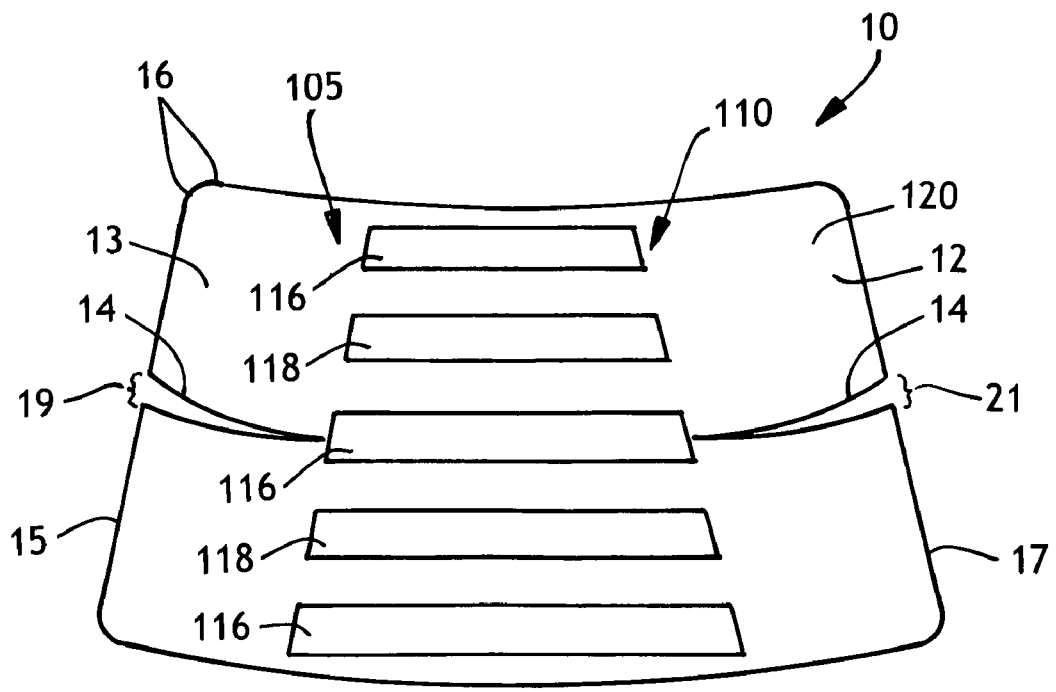
FIG. 2 is a plan view of the article shown in FIG. 1 with cuts in the body of the article separated.

As shown in FIG. 2, the body 12 of the article 10 is separable at the cuts 14. In the example aspect illustrated in FIGS. 1 and 2, the body 12 includes a perimeter 16 and the cuts 14 extend into the body 12 from the perimeter 16 of the body 12.

Figure 3:
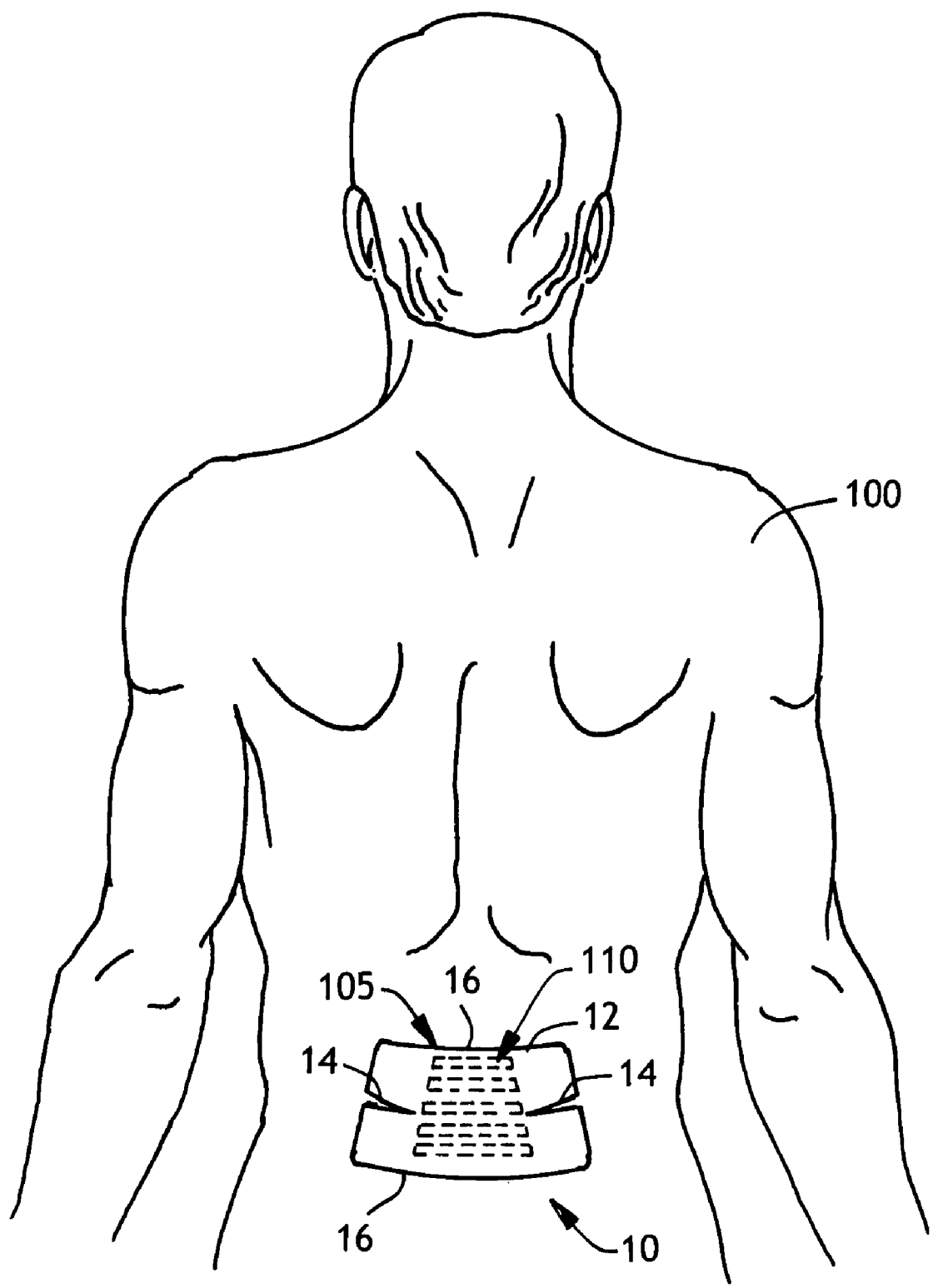
FIG. 3 is a plan view illustrating the article shown in FIGS. 1 and 2 mounted onto an individual.

FIG. 3 illustrates that when the article 10 is applied to an individual 100, the cuts 14 may give the article 10 more flexibility in the area of the cuts 14. The increased flexibility of the article 10 at the cuts 14 may allow the article 10 to fit more readily onto a highly contoured area of the individual 100. Structures such as the cuts 14 are not necessary for the functioning of the article 10 and may be omitted from the article 10 without affecting this disclosure.

Referring again to FIGS. 1 and 2, the body 12 may be comma-shaped and include a first end 15 and a second end 17. A first cut 14 may extend into the body 12 from a midsection 19 of the first end 15 and a second cut 14 may extend into the body 12 from a midsection 21 of the second end 17.

Although body 12 is shown as being shaped somewhat arcuately in FIGS. 1 and 2, it should be noted that body 12 may be other shapes and/or sizes. The proper size and shape of the article 10 will depend on the application where the article 10 is used. In some forms, the article 10 may be long enough to fit around the arms, legs, head, or torso of an individual's body.

As used herein, patch refers to any type of patch, pack, bag, or pouch that may be used to apply therapy to a body. In addition, article 10 may be capable of being attached directly, or indirectly, to an individual.

In other aspects, the cuts 14 may be formed by slicing the body 12 of the article 10. It should be noted that the cuts 14 may be linear, curved, comma-shaped or any other shape that facilitates mounting the article 10 onto an individual 100.

Figure 4:
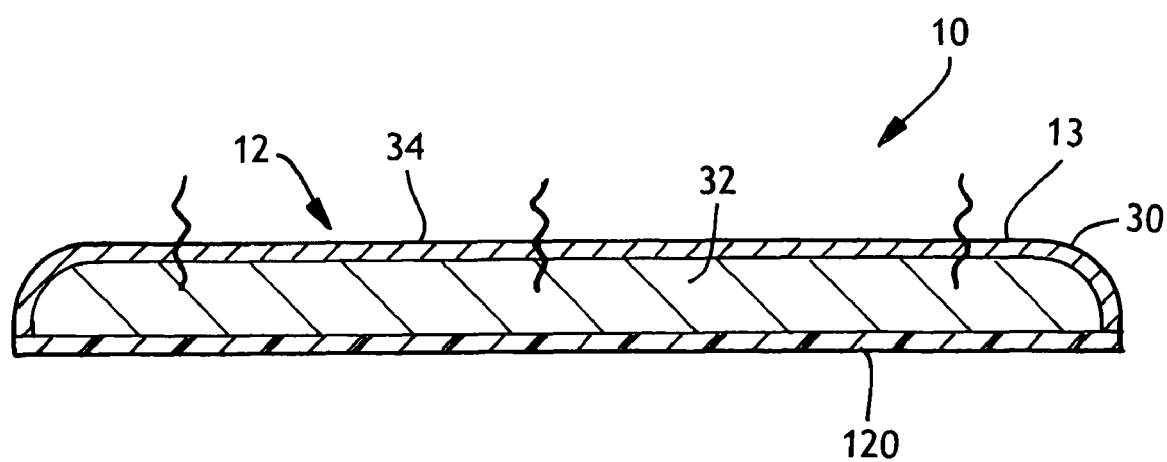
FIG. 4 is a section view of the article shown in FIG. 1 taken along line 4-4 illustrating an example aspect where the article is a heat patch.

FIG. 4 illustrates an example aspect where the article 10 is a heat patch that may be used to apply heat therapy to an individual 100. In some forms, the body 12 of the heat article 10 may include an enclosure 30 and a heating composition 32 that is sealed inside the enclosure 30. The heating composition 32 is a heat generator and may be capable of generating heat when a gas, such as oxygen contained in ambient air, is received through a gas-permeable section 34 of the enclosure 30.

When the article 10 is a heat patch, it may be stored in a hermetic environment (e.g., a sealed bag) such that the heating composition remains inactive until the heat patch is removed from the hermetic environment. Once the article 10 is removed from the hermetic environment, the heating composition 32 within the enclosure 30 is exposed to air such that an exothermic reaction takes place within the body 12 of the heat article 10. The exothermic reaction generates heat within the article 10 to increase the temperature of the article 10.

Any conventional heating composition may be used to induce an exothermic reaction within article 10. Some example heating compositions include iron powder as the main active ingredient. Alternatively, the article 10 may include as a heat generator any suitable electrical heating system. Also alternatively, the article 10 may include as a heat generator any suitable fluid, gel, or solid heat storage system that can be heated in a microwave oven, in a conventional oven, in a water bath, or by any other suitable means.

FIGS. 1 and 2 further illustrate an example system 105 for delivering a heating sensation. The system 105 includes a thermal grill 110 that can create the perception of heat when an individual touches the thermal grill 110. In one aspect of the present disclosure, the thermal grill 110 is maintained in at least partial skin contact with a wearer of the article 10 due to the positioning of the thermal grill 110 on a skin-facing surface 120 of the body 12. It should be noted that the thermal grill 110 may be any suitable type of thermal grill.

While a single thermal grill 110 is shown in the illustrated aspect, it is contemplated that additional thermal grills 110 may be used to further enhance the perception of heat by the wearer.

In one aspect of the present disclosure, warm and cool portions 116, 118 of the thermal grill 110 are formed by applying alternating stripes of endothermic and exothermic sources to the skin-facing surface 120 of the article 10. In various aspects of the present disclosure, the endothermic and exothermic sources may be applied to the skin-facing surface 120 by blending the endothermic and exothermic sources into a lotion or other substance which is then applied to one of the structural layers. In another aspect of the present disclosure, the endothermic and exothermic sources may also be combined into a liquid concentrated solution and sprayed onto the skin-facing surface 120. In still another aspect of the present disclosure, the endothermic and exothermic sources may be produced in crystalline form and sprinkled or otherwise applied to the skin-facing surface 120, using a suitable adhesive if desired. In any of these aspects, the endothermic and exothermic sources may be applied in alternating stripes, a checkerboard pattern, a concentric pattern of aligned circles or other shapes, or any other suitable geometric or non-geometric pattern. Similarly, different warm and/or cool portions 116, 118 may be colored using inks, dyes, or any other suitable substance. Finally, the endothermic and/or exothermic sources may be combined with an additives such as clay or a phase change material such as a wax or low molecular weight polymer to increase the duration of cooling/heating.

For the aspect in which at least one of the warm and/or cool portions 116, 118 relies on a chemical reaction, that portion of the thermal grill can be activated in a number of ways. The user may apply water or other liquid to the skin-facing surface 120. Water or other liquid may be encapsulated or microencapsulated and disposed between the skin-facing surface 120 and a peel strip (not shown) applied to the skin-facing surface 120. When a user removes the peel strip, the capsules rupture and provide water or other liquid to the thermal grill. Water or other liquid may be supplied from a bodily exudate, or from moisture resident in a user's skin. The user may need to activate a self-contained ice pack. Any other suitable source of water or other liquids may be used.

For the aspect in which at least one of the warm and/or cool portions 116, 118 relies on an electrical or mechanical device, that portion of the thermal grill can be activated in a number of ways. The user may operate a switch to complete a circuit to supply electricity to that portion. The user may open valves leading to a source of warm or cool fluid.

The endothermic and exothermic sources may be suitably responsive to contact with an aqueous solution, such as water, to either absorb or release heat. The mechanism by which these are accomplished may be the dissolution of the endothermic and exothermic sources in the aqueous solution, the swelling of the endothermic and exothermic sources in the aqueous solution, and/or the reaction of the endothermic and exothermic sources in the aqueous solution. In particular aspects, the endothermic and exothermic sources are suitably in the form of particles that have a substantial energy difference between a dissolved state and a crystalline state, so that energy in the form of heat is absorbed or released to the environment upon contact with an aqueous solution such as water. In other aspects, the endothermic and exothermic sources release or absorb energy during swelling or reacting of the endothermic and exothermic sources with an aqueous solution such as water.

Other mechanisms/effects that can be used as endothermic and/or exothermic sources include heat of reaction, heat of crystallization, heat of hydration, heat of oxidation, acid/base chemistry, nuclear, electrical resistance, non-contact wave energy (such as RF, microwave, etc), heat pipe technology, Peltier devices, and the like, and suitable combinations thereof.

While a wide variety of endothermic and exothermic sources may result in a temperature change in response to contact with an aqueous solution, the selection of a particular endothermic or exothermic source and the determination of the amount to be used is based at least in part on the desired temperature change to be experienced by the wearer. Endothermic and exothermic sources suitable for use in the article 10 include those that dissolve in an aqueous solution. The solubility of such endothermic and exothermic sources are suitably in the range of about 0.1 to about 3 grams of water ($H_2O$) per gram of agent (g/g), and more particularly from about 0.1 to about 2 g/g.

In various aspects of the present disclosure, the cool portions 118 may be formed using suitable endothermic sources that absorb heat during dissolution upon contact with an aqueous solution including, without limitation, salt hydrates such as sodium acetate, sodium carbonate, sodium sulfate, sodium thiosulfate, and sodium phosphate; anhydrous salts, such as ammonium nitrate, potassium nitrate, ammonium chloride, potassium chloride, sodium bromide, magnesium sulfate, and sodium nitrate; organic compounds, such as urea and acetone; carbohydrates such as xylitol, dextrose, and other sugars; and any other suitable sources.

The endothermic source can also include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued to Greenberg, and U.S. Pat. No. 5,266,592 issued to Grub et al.

In various aspects of the present disclosure, the warm portions 116 may be formed using suitable exothermic sources that release heat during dissolution including, without limitation, metal-halogen compounds such as aluminum chloride, magnesium chloride, calcium chloride, and manganese iodide; salts such as aluminum sulfate and potassium aluminum sulfate; metal hydroxides such as calcium oxide, barium oxide, and phosphorous pentoxide; and any other suitable source.

The endothermic and exothermic sources may also, or may instead, include a material that absorbs or releases heat during swelling upon contact with aqueous solution. By way of illustration, one suitable material that releases heat during such swelling is a polymer such as lightly cross-linked partially neutralized polyacrylic acid. Alternatively, or additionally, the endothermic and exothermic sources may include a material that absorbs or releases heat upon reaction with an aqueous solution.

In yet another aspect of the present disclosure, the endothermic and exothermic sources may be applied on separate structural layers of the article 10. For example, the exothermic source can be applied to the skin-facing surface 120, and the endothermic source can be applied to an additional layer (not shown) under the skin-facing surface 120.

In still another aspect of the present disclosure, a covering layer of any suitable material may be interposed between part or all of the thermal grill 110 and the skin of the wearer if skin contact with the thermal grill 110 is desired to be limited. Suitable materials include those for use in the article 10. In addition, suitable materials may be fluid permeable and at least somewhat temperature-conductive.

In another aspect of the present disclosure, the skin-facing surface 120 or the additional layer may include a suitable skin adhesive to enhance contact between the thermal grill 110 and the wearer's skin.

In another aspect of the present disclosure, the ability to vary the thermal grill effect for different levels of heating has application in providing varying levels of therapy. For example, one set of articles 10 or other products with thermal grills 110 exhibiting little heating may be provided for individuals with sensitive skin, while another set of articles 10 with thermal grills 110 exhibiting higher levels of heating may be provided for individuals with normal or more insensitive skin.

The endothermic and exothermic sources are essentially temperature-neutral when resident on the article 10. The endothermic and exothermic materials do not have a cooling or warming effect before the article 10 is donned by the wearer. It is only upon activating that endothermic and exothermic sources react and exhibit cooling and warming effects, respectively. Once the warm and cool portions 116, 118 are activated, the thermal grill effect is activated, resulting in the individual, whose skin is in contact with the thermal grill 110, feeling a heating sensation. Thus, the thermal grill 110 may be activated by liquid provided by the wearer of the article 10.

In another aspect of the present disclosure, the warm and cool portions 116, 118 of the thermal grill 110 are formed using Peltier devices configured to alternately form the warm and cool portions 116, 118. Peltier devices are known in the art and create a heat different from electricity. A current is passed through two dissimilar metals or semiconductors that are connected to each other at two junctions. The current drives a heat transfer from one junction to the other. As a result, one junction becomes the hot side as it increases in temperature while the other junction becomes the cold side as it is reduced in temperature. Positioning Peltier devices with alternating hot and cold sides creates warm and cool portions 116, 118 and therefore a thermal grill 110. In another aspect of the present disclosure, the Peltier device has a first setting exhibiting a first temperature difference between the warm and cool portions when activated and a second setting exhibiting a second temperature difference between the warm and cool portions when activated. In this aspect, the second temperature difference is greater than the first temperature difference, yielding a more intense heating sensation with the second setting.

In still another aspect of the present disclosure, the warm and cool portions 116, 118 of the thermal grill 110 are formed using mechanical structures configured to alternately form the warm and cool portions 116, 118. For example, the warm and cool portions 116, 118 may be alternating channels such as tubes or pipes in which reside or through which flow warm and cool fluids, respectively. Warm and cool fluids may be supplied from external sources as is known in the art.

In yet another aspect of the present disclosure, the warm and cool portions 116, 118 of the thermal grill 110 are formed using an electrical resistance heater for the warm portion 116, and a self-contained chemical cooling pack for the cool portions 118. In another aspect of the present disclosure, the warm and cool portions 116, 118 of the thermal grill 110 are formed using an electrical resistance heater for the warm portion 116, and the cold side of Peltier junctions pack for the cool portions 118. In another aspect of the present disclosure, the warm and cool portions 116, 118 of the thermal grill 110 are formed using the hot side of Peltier junctions for the warm portion 116, and a fan for cooling the cool portions 118. In various other aspects of the present disclosure, the warm and cool portions 116, 118 may be provided using any combination of the aspects described herein, or using any other suitable alternatives.

In other aspects of the present disclosure (not shown), a thermal grill may be arranged by any of the aspects described herein on a skin-facing surface 120 as a stand-alone insert usable with any garment or article including clothing, towels, covers, and absorbent articles. In these aspects, the thermal grill is arranged as described above with the exception that the remainder of a patch other than a skin-facing surface 120 is not present. In addition, the skin-facing surface 120 may be coupled to a backing layer or layers by any suitable means. Also, the insert may include means to attach the insert to a garment or other article such as adhesive, hook, loop, snaps, elastic, folds, buttons, pins, any other suitable attachment means, or a combination of these.

In the insert aspect of the present disclosure, the user of a garment or other article or the caregiver of the user positions the insert including a thermal grill within the user's garment or other article.

In many of these aspects, a heat generator is supplied to provide long-term heating. Because most such heat generators are relatively slow to achieve their operating temperatures, a thermal grill 110 provides an instant-on sensation of heat to the user while the heat generator is achieving its operating temperature.

In various aspects of the present disclosure, the system 105 may include informational items such as instructions in the use of the product and tips for therapy or comfort. As used herein, the term "informational item" refers to objects that are provided in addition to articles such as the article 10, are adapted to communicate information to the user and/or consumer of the training article, and are associated with individual components of the system 105. Examples of informational items include cards, paper, electronic media, printing on the packaging, or other suitable media capable of storing and conveying information.

In various aspects, the informational items associated with the system components may be adapted to appeal to the specific category of user and/or purchaser to which the product is adapted. The informational items may be adapted, for example, by providing information likely to be of interest to a given category of user and/or purchaser.

For example, a product may be adapted for use by a caregiver for therapy purposes. An informational item may be associated with the product that is adapted to interest caregivers. For example, the informational item may be a card containing information or instructions about a patient's health and hygiene, such as exercise, sleep habits, skin health, questions to ask a patient, jokes, and the like, and combinations thereof. The informational item may additionally or alternatively include addresses for web sites available on the Internet. The web sites may contain information related to issues of interest for caregivers and users of such products.

The informational item may additionally or alternatively include information describing activities that are suitable for caregivers and users of such products. The activities may be adapted for a patient at a specific age, size, and/or stage of development. For example, the activities may be adapted to promote interaction between the patient and the caregiver.

The informational item may additionally or alternatively include information describing the benefits to be derived from using the system 105. This informational item would be part of a promotional plan emphasizing the customizability of the system 105 for the benefit of the consumer, caregiver, and/or user. This informational item would both explain the use of the various components of the system 105 as well as present the additional components that may be available and the various combinations that are possible to achieve different goals.

EXAMPLE 1

A thermal grill using materials such as those described above was constructed. Alternating areas of warm and cool portions were established using XYLISORB xylitol 700 Batch E0929, available from Roquette America Inc., as the endothermic material and calcium chloride in the form of DAMPRID moisture controller, available from DampRid, Inc., as the exothermic material, where the calcium chloride was crushed to approximately the same particle size as that of the endothermic material. The endothermic and exothermic materials were sandwiched between two sheets of a perforated film nonwoven material available from Tredegar. Each area of material was approximately 38 mm by 10 mm and contained approximately 1.5 grams of material per area. The areas were separated by approximately 3 mm (in which there was no endothermic or exothermic material). There were four areas of each material, again in an alternating arrangement.

The thermal grill was then sprayed with warm water to dissolve the endothermic and exothermic materials. Enough water was used to obtain a noticeable temperature change in the endothermic and exothermic materials. The warm and cool portions were tested using a single finger tip to make sure the endothermic and exothermic chemistries were working as desired and expected.

A test subject placed his right forearm on the thermal grill and immediately felt a sensation of "heat" that was much greater than sensation felt on any of the individual warm portions. A second, identical thermal grill was prepared, and a second test subject felt an identical sensation using his hand. Both test subjects reported that the sensation of heating was pronounced but not long lasting once skin contact ended. Neither test subject experienced skin damage or any physical effects.

EXAMPLE 2

A thermal grill using materials such as those described above was constructed. Alternating areas of warm and cool portions were established using XYLISORB xylitol 700 Batch E0929, available from Roquette America Inc., as the endothermic material and magnesium chloride as the exothermic material. The magnesium chloride was crushed to approximately the same particle size as that of the endothermic material and then mixed in a proportion of one part magnesium chloride to three parts Laponite SMF (CP1334) clay, available as sample reference #2093 from Rockwood Additives in Widnes, Cheshire, Great Britain. The endothermic and exothermic materials were sandwiched between two sheets of a perforated film nonwoven material available from Tredegar. Each area of material was approximately 38 mm by 10 mm and contained approximately 1.5 grams of material per area. The areas were separated by approximately 3 mm (in which there was no endothermic or exothermic material). There were four areas of each material, again in an alternating arrangement.

The thermal grill was then sprayed with warm water to dissolve the endothermic and exothermic materials. Enough water was used to obtain a noticeable temperature change in the endothermic and exothermic materials. The warm and cool portions were tested using a single finger tip to make sure the endothermic and exothermic chemistries were working as desired and expected. The addition of clay to the exothermic material appeared to increase the duration of heating by the exothermic material.

Test subjects in a single-blind manner placed their forearms on the thermal grill and immediately felt a sensation of "heat" that was much greater than sensation felt on any of the individual warm portions. All test subjects reported that the sensation of heating was pronounced but not long lasting once skin contact ended. Test subjects experienced no skin damage or any physical effects.

EXAMPLE 3

A thermal grill using materials such as those described above was constructed. Alternating areas of warm and cool portions were established using warmed and cooled water circulating in copper piping. Quarter-inch copper pipes were arranged in an alternating array of 12 warm and 12 cool pipes. Pipes were an elongated U-shape with one set 1 inch high and 5.5 inches wide with the other set 1 inch high and 7.5 inches wide. The pipes were soldered into 0.75 inch by 0.75 inch steel manifolds to provide common entry and common exit of the water.

Warm water was produced with a Precision Model Number 281 water bath from Precision Scientific, Inc. Cold water was produced with the addition of ice to a beaker of water until a given temperature was produced. The water was pumped with a MASTERFLEX peristaltic pump available from Cole Palmer: Model Number 7550-10 manufactured by the Barnant Company of Barrington, Ill. The pump size used was 7024-21. Temperatures were measured with surface mounted Type K thermocouples read by a DIGI-SENSE Scanning Digital Thermometer Model Number 92800-10 manufactured by the Barnant Company, Barrington, Ill., and adjusted until the thermal grill effect was apparent.

Test subjects placed their forearms on the thermal grill and immediately felt a sensation of "heat" that was much greater than sensation felt on any of the individual warm portions. All test subjects reported that the sensation of heating was pronounced but not long lasting once skin contact ended. Test subjects experienced no skin damage or any physical effects.

While the disclosure has been described in detail with respect to the specific aspects thereof, it will be appreciated that those skilled in the art, upon attaining an understanding of the foregoing, may readily conceive of alterations to, variations of, and equivalents to these aspects that fall within the spirit and scope of the present disclosure, which should be assessed accordingly to that of the appended claims.

We claim:

1. An article adapted to produce heat, the article comprising:
   an outer surface having a skin-facing surface, the outer surface enclosing a heat generator; and
   a thermal grill disposed on the skin-facing surface.

2. The article of claim 1, wherein the heat generator includes a heat-producing chemical reaction.

3. The article of claim 1, wherein the heat generator includes an electrical heat source.

4. The article of claim 1, wherein the heat generator includes a heat-storing substance.

5. The article of claim 1, wherein the skin-facing surface includes a skin-compatible adhesive.

6. The article of claim 1, wherein the thermal grill includes a cool portion having an endothermic source and a warm portion having an exothermic source.

7. The article of claim 6, wherein the endothermic source is a carbohydrate.

8. The article of claim 7, wherein the carbohydrate is xylitol or dextrose.

9. The article of claim 6, wherein the endothermic source is a salt hydrate.

10. The article of claim 9, wherein the salt hydrate is sodium acetate, sodium carbonate, sodium sulfate, sodium thiosulfate, or sodium phosphate.

11. The article of claim 6, wherein the endothermic source is an anhydrous salt.

12. The article of claim 11, wherein the anhydrous salt is ammonium nitrate, potassium nitrate, ammonium chloride, potassium chloride, sodium bromide, magnesium sulfate, or sodium nitrate.

13. The article of claim 6, wherein the endothermic source includes a fan.

14. The article of claim 6, wherein the endothermic source is a ketal.

15. The article of claim 6, wherein the exothermic source is a metal-halogen compound.

16. The article of claim 15, wherein the metal-halogen compound is aluminum chloride, magnesium chloride, calcium chloride, or manganese iodide.

17. The article of claim 6, wherein the exothermic source is a salt.

18. The article of claim 17, wherein the salt is aluminum sulfate or potassium aluminum sulfate.

19. The article of claim 6, wherein the exothermic source is a metal hydroxide.

20. The article of claim 19, wherein the metal hydroxide is calcium oxide, barium oxide, or phosphorous pentoxide.

21. The article of claim 6, wherein the exothermic source is a polymer.

22. The article of claim 6, wherein the exothermic source is an electrically-resistive element.

23. The article of claim 6, wherein one of the warm and cool portions includes a filler material.

24. The article of claim 1, wherein the thermal grill is an alternating pattern of cool portions and warm portions.

25. The article of claim 1, wherein the thermal grill has a cool portion including a cold side of a Peltier device and a warm portion including a hot side of a Peltier device.

26. The article of claim 25, the Peltier device having
   a first setting exhibiting a first temperature difference between the warm and cool portions when activated; and
   a second setting exhibiting a second temperature difference between the warm and cool portions when activated; wherein the second temperature difference is greater than the first temperature difference.

27. The article of claim 1, wherein the thermal grill has cool and warm portions each including a fluid-accommodating channel.

28. The article of claim 1, wherein the thermal grill includes a covering layer.

* * * * *